(12) United States Patent
Smith et al.

(10) Patent No.: US 7,705,339 B2
(45) Date of Patent: Apr. 27, 2010

(54) PORTABLE REACTOR FOR REAL-TIME NUCLEIC ACID AMPLIFICATION AND DETECTION COMPRISING A REACTION CHAMBER FORMED FROM A FLEXIBLE PRINTED CIRCUIT BOARD

(75) Inventors: Matthew C. Smith, St. Petersburg, FL (US); David Fries, St. Petersburg, FL (US); George Steimle, St. Petersburg, FL (US); Stanislav Ivanov, St. Petersburg, FL (US)

(73) Assignee: University of South Florida, Tampa, FL (US)

( * ) Notice: Subject to any disclaimer, the term of this patent is extended or adjusted under 35 U.S.C. 154(b) by 5 days.

(21) Appl. No.: 11/739,993

(22) Filed: Apr. 25, 2007

(65) Prior Publication Data

US 2008/0128597 A1    Jun. 5, 2008

Related U.S. Application Data

(60) Provisional application No. 60/745,545, filed on Apr. 25, 2006.

(51) Int. Cl.
*G01N 15/06* (2006.01)
*C12M 1/38* (2006.01)

(52) U.S. Cl. ................... 250/576; 435/303.1
(58) Field of Classification Search ........... 250/239, 250/458.1, 238, 576; 435/288.7, 288.5, 303.1; 356/340, 246, 349, 442; 422/68.1, 58, 100, 422/63, 102, 82.12, 82.07, 82.08, 52, 99; 436/180, 172
See application file for complete search history.

(56) References Cited

U.S. PATENT DOCUMENTS

| | | | | |
|---|---|---|---|---|
| 4,974,591 | A * | 12/1990 | Awazu et al. | 600/344 |
| 5,589,136 | A * | 12/1996 | Northrup et al. | 422/102 |
| 6,312,886 | B1 * | 11/2001 | Lee et al. | 435/4 |
| 6,403,037 | B1 * | 6/2002 | Chang et al. | 422/68.1 |
| 6,440,725 | B1 * | 8/2002 | Pourahmadi et al. | 435/288.5 |
| 6,444,462 | B1 * | 9/2002 | Pfeifer et al. | 435/303.1 |
| 7,186,989 | B2 | 3/2007 | Farmer et al. | |
| 2004/0108197 | A1 * | 6/2004 | Buhr | 204/157.15 |
| 2005/0269522 | A1 * | 12/2005 | Farmer et al. | 250/458.1 |
| 2006/0057771 | A1 * | 3/2006 | Kovacs et al. | 438/106 |

OTHER PUBLICATIONS

Farmer, Andrew S., David P. Fries, William Flannery, and John Massini. 2005. Hand-Held Thermal-Regulating Fluorometer. Rev. Sci. Instrum. 76, 115102 1-5.

* cited by examiner

*Primary Examiner*—Que T Le
*Assistant Examiner*—Jennifer Bennett
(74) *Attorney, Agent, or Firm*—Michele L. Lawson; Smith & Hopen, P.A.

(57) ABSTRACT

The present invention provides core technologies necessary for a portable, low cost LED-based handheld fluorometer. The fluorometer is based on a heater integrated within the walls of the reaction chamber, and an orthogonal geometry LED based light source to provide optical excitation. Power is supplied through either an internal power supply, and data is collected in real-time through standard serial interfaces of personal computers, which can also be used to provide power, or personal digital assistants. Thermal regulation is automatically maintained using temperature sensor feedback control. Such a handheld system can allow applications requiring temperature sensitive photometric measurements for real time analyte detection to be performed in the field.

15 Claims, 8 Drawing Sheets

PORTABLE REACTOR FOR REAL-TIME NUCLEIC ACID AMPLIFICATION AND DETECTION COMPRISING A REACTION CHAMBER FORMED FROM A FLEXIBLE PRINTED CIRCUIT BOARD

CROSS REFERENCE TO RELATED APPLICATIONS

This application claims priority to U.S. Provisional Application 60/745,545, filed Apr. 25, 2006; which is incorporated herein by reference.

STATEMENT OF GOVERNMENT INTEREST

This invention was made with Government support under Grant No. DASG60-00-C-0089 awarded by the U.S. Army, Space Missile Defense Command. The Government has certain rights in the invention.

BACKGROUND OF THE INVENTION

The advent of molecular biological techniques has led to a dramatic increase in the speed, efficiency and species resolution obtained in microbiological studies from virtually every environment on earth. While this has revolutionized the way microbiology is performed, a requirement for access to laboratory facilities and infrastructure still exists, thereby introducing a spatial and temporal separation between sample collection and analysis.

There has been an increasing need in the scientific and military communities to collect and analyze data in the field. In situ analysis holds many advantages over collecting samples, transporting them, and analyzing the samples in a laboratory. Timely analysis reduces degradation of the samples, permits more rapid feedback to the observer, and may reduce overall cost as well as improve the results of the analysis.

Toward achieving a truly portable sensor, several requirements must be kept in mind. The system must be operated on an internal battery or portable power; therefore the entire system must be conservative with its power usage in order to be operable for an extended period of time. There should be a method for giving feedback to the user, in order to verify the analysis is being performed properly. Preferably, a familiar graphical user interface (GUI) should be provided to display the data or other relevant information in real-time, this will allow the user to immediately interpret and react to the test results. In addition to displaying information, the data should be stored for later retrieval and further analysis on a desktop computer. To achieve widespread use, the system cost should be kept as low as possible. This is especially relevant for MEMS sensors, which take advantage of wafer-level processing capabilities, to reduce the cost of system components. To be truly portable and easily operated by the end user, the complete sensor assembly should be handheld.

As is known in the art, a filter fluorometer measures the ability of a sample to absorb light at one wavelength and emit light at a longer wavelength. A filter fluorometer is a good choice when sensitive quantitative measurements are desired for specific compounds. The comparative ease of handling and low cost make filter fluorometers ideal for dedicated and routine measurements. A fluorometer provides a relative measurement and can be calibrated with a known concentration standard or correlated to standard laboratory methods to produce quantitative measurements. Fluorometers are utilized in molecular biology for the detection and measurement of a variety of elements. In a particular application, it is known to use a filter fluorometer as a nucleic acid amplification device.

Due to the temperature sensitivity of fluorescence measurements, many fluorometers include heating and cooling capabilities. Heating systems know if the art for use in fluorometers, consist of ceramic block or resistive heaters and cooling fans. These components exhibit a high thermal mass.

Common bench top instrumentation platforms, including filter fluorometers, are large and expensive, and primarily target high throughput screening laboratory analysis. Such systems offer little recourse for laboratories operating on limited budget, tight space restrictions, small sample throughput, or to technicians collecting samples in the field. Environmental and clinical applications that require nucleic acid amplification, enzymatic studies and analytical biochemical reactions, that require precise thermal control, would benefit from a portable instrumentation system designed for these applications.

System in Package (SiP) design methodology in the electrical packaging field takes advantage of the integration of high degrees of chip scale packages onto interconnect substrates to develop novel compact electronic systems. SiP has numerous advantages over other packaging design paradigms such as System on Chip (SoC) where complete electronic systems are integrated onto a single chip. Typically SiP decreases design risk, developmental time and cost compared to SoC systems as each individual component is manufactured in its own optimised process and interfering components can be more easily isolated from each other during the design and manufacturing process. Similarly SiP systems provide more flexible design which allows for easy modification to circuitry when advances in processor speeds or memory occur. SiP delivers increased functionality and performance in a small form factor for mobile applications. As such, SiP has become the leading mechanism for the miniaturization and added functionality of consumer electronics such as laptop computers, mobile phones and portable music players, however, it has not been aggressively applied in the design and miniaturization of portable scientific equipment.

Compared to traditional culturing and biochemical analysis, molecular detection techniques such as the Polymerase Chain Reaction (PCR) or Nucleic Acid Sequence Based Amplification (NASBA) have dramatically decreased the time required to analyse samples from virtually any environment. Point-of-use real-time molecular detection techniques have the potential to remove the spatial and temporal separation between sample collection and analysis that exists in standard laboratory practices. However, despite many molecular assays being adaptable to in-field use, at present the majority still reside in the laboratory, primarily due to a lack of small, cheap and portable instrumentation.

A portable hand-held heat regulated fluorometer capable of performing and detecting Real-Time (RT)-NASBA was previously developed used a commercially available infra-red heater and detector for thermal control and had relatively high power requirements. Various iterations of the instrument have been developed, however to date all have required an expensive user interface such as a personal computer or Personal Data Assistant (PDA).

Therefore, what is needed is a simplified and compact hand-held instrument to perform, detect and report a RT-NASBA reaction, as a demonstration for portable isothermal amplification and detection.

SUMMARY OF INVENTION

In an illustrative embodiment, the invention includes a low thermal mass fluorometer, the fluorometer comprising a reaction chamber, a heater integrally formed with the reaction chamber, a reaction vessel suspended within the reaction chamber (positioned to leave a space between the reaction vessel and the reaction chamber), a light emitting diode positioned to supply fluorescence excitation to the reaction chamber (positioned geometrically orthogonal to the reaction vessel) and a photodetector positioned to detect fluorescence emission from the reaction chamber. The device also includes a control software module in circuit communication with the temperature feedback controller, the light emitting diode and the integrated photodetector.

In a preferred embodiment, the reaction chamber is formed from a flexible printed circuit board substrate, such as a liquid crystal polymer printed circuit material. Circuitry for the heater, light emitting diode and photodetector are etched into the liquid crystal polymer material.

The fluorometer of a preferred embodiment can be run with an internal or external power supply. A serial communication module is also adapted in circuit communication with the photodetector. There is also an output display in communication with the serial communication module.

In one embodiment, the photodetector is a 567 nm reflective green color sensor and the light emitting diode is a 470 nm blue light emitting diode. The resistive heater of a preferred embodiment is a MEMS-based linear resistive temperature device comprising a plurality of connected, concentric traces formed in the exterior of the reaction chamber. The traces formed in the exterior of the reaction chamber are about 120 µm wide. The resistance of the heater is about $\geqq 5\Omega$. The reaction vessel is a glass waveguide capillary with the end thereof formed into a semi-spherical ball lens.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

In one embodiment, the invention includes a compact heated fluorometer formed from folded flexible printed circuit board (PCB) substrate to produce a 3-dimensional reaction chamber, using planar fabrication techniques and component placement. The mini-fluorometer uses an integrated heater/detection chamber manufactured from Liquid Crystal Polymer (LCP) printed circuit material. Circuits for a planar resistive heater, integrated LED and filtered photo-detector are etched into the LCP material using photolithography and printed circuit board manufacturing techniques.

Figure 1:
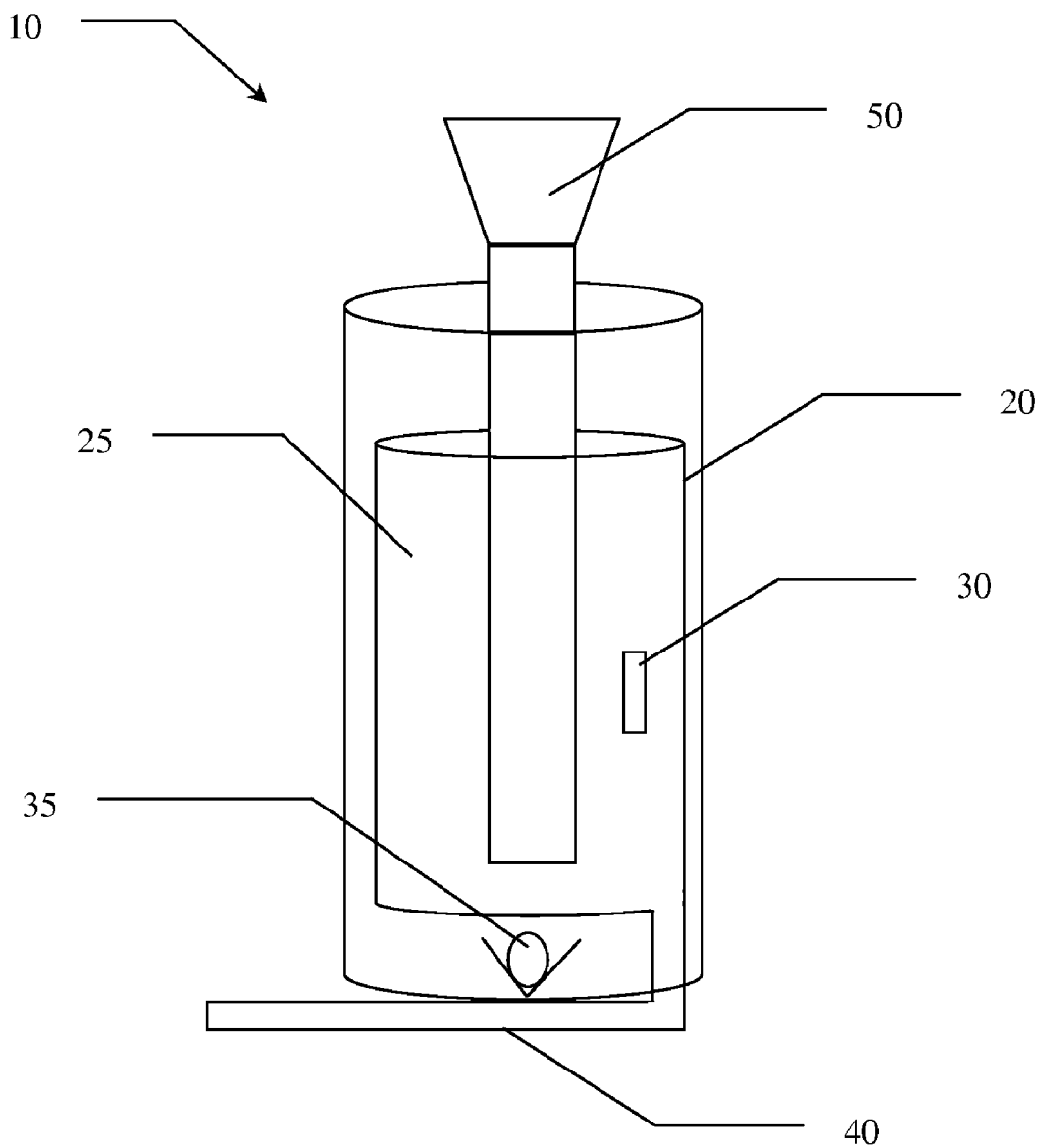
FIG. 1 is a block diagram of the folded form-factor and schematic representation of the mini fluorometer.

FIG. 1 illustrates the relative positioning of the elements of the fluorometer in accordance with the present invention. As shown, fluorometeer 10 includes heater/detection chamber 20, which is manufactured as a planar circuit, with light source 30 and photo detector 35 attached. The planar circuit is then folded in space to form cylindrical reaction/detection chamber 20. Heat is both supplied and regulated by measuring the resistance of the heater circuit 25, which is integrally formed on the outer face of chamber 20, at a constant voltage and varying current. RT-NASBA is performed in the device using commercially available disposable glass waveguide capillary 50 as the reaction vessel. Capillary 50 is suspended within chamber 20 such that a space exists between it and the chamber wall. The air-capillary interface allows internal reflection along the capillary wall according to Snell's Law. The end of capillary 50 is formed into a hemi-spherical ball lens that aids in focusing fluoresced light from the RT-NASBA reaction onto photo-detector 35 at the base of chamber 20. Excitation light is supplied orthogonal to the capillary through light source 30. Connective ribbon 40 provides communication with electrical devices such as personal computers, laptops and personal digital assistants (PDAs).

While the miniature SiP fluorometer is the core of the handheld analyzer, the device of a preferred embodiment contains a series of indicators, such as LEDs, that advise the user of a positive or negative result thereby negating the need for an expensive external user interface. For more in-depth analysis, data is concurrently stored to FLASH memory and can be downloaded to a personal computer; such as with a USB connection.

Power is supplied by an internal source, such as an integrated 3 V lithium ion battery, or via and external source such as a USB connection. This configuration improves flexibility for field application, or in areas with limited laboratory infrastructure. The hand-held device has application in environmental and medical monitoring in remote areas where access to traditional laboratory equipment is impractical or unaffordable or in bio-defense scenarios where rapid assessment is required.

Reaction/Detector Chamber Construction

Figure 2A:
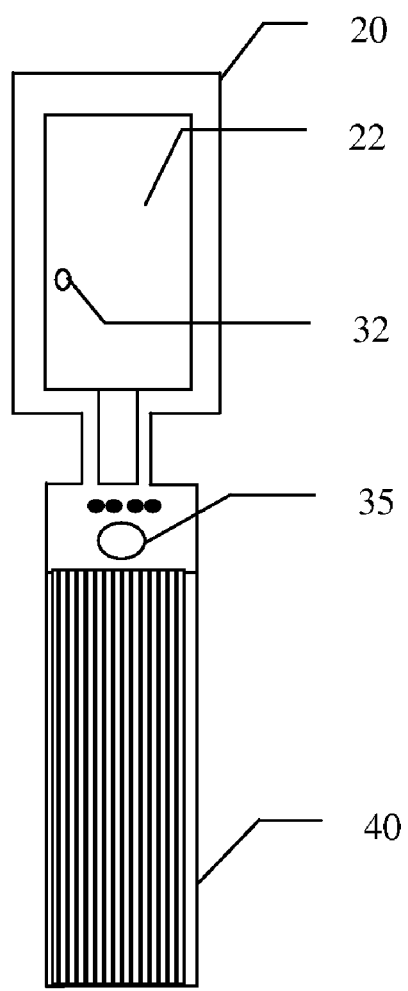
FIG. 2A: is a planar views of the mini-fluorometer circuit, showing the internal facing side with attached photo-detector, via containing the mounted LED and integrated ribbon connector.
Figure 2B:
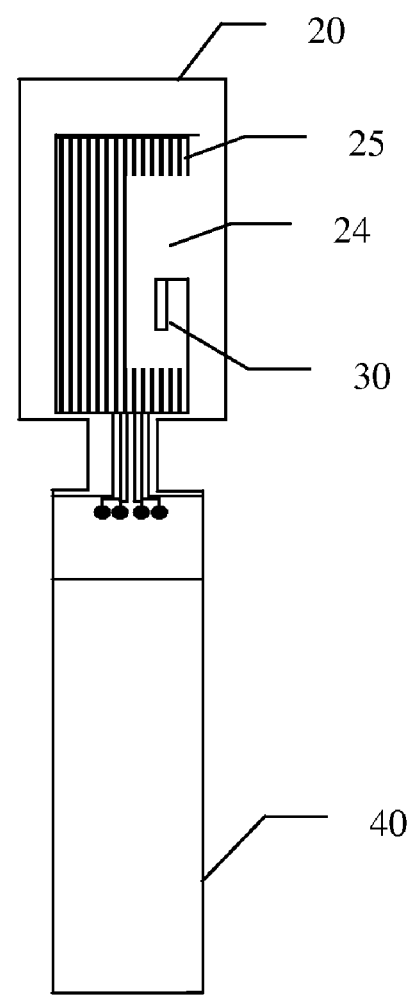
FIG. 2B is a planar views of the mini-fluorometer circuit, showing the externally facing resistive heater with rear mounted LED.

The following is a description of a specific embodiment in accordance with the present invention. FIGS. 2A and 2B highlight the construction of the 3-Dimensional fluorometer from planar circuitry. In FIG. 2A the inner surface 22 of reaction chamber 20 can be seen. Through-hole 32 allows light from source 30 to enter the chamber orthogonal to the reaction vessel (not shown). Photo-detector 35 is integrally formed with conductive ribbon 40 such that it will be below chamber 20 when the planar circuitry is folded to form the 3-Dimensional fluorometer. FIG. 2B shows outer surface 24 of reaction chamber 20 with the integrated circuitry for heather 25 disposed thereon. Light source 30 is also integrally formed on outer surface 24 adjacent to through hole 32 (FIG. 2A).

Artwork for the front and back circuits of reaction/detection chamber 20 is imaged onto green reversal film, such as by mask-less photolithography. Reaction/detection chamber 20 is constructed from 0.05 mm double sided copper bonded LCP, by drilling a series of 4, 0.254 mm holes into the LCP. Electroless- and electro-copper deposition was then used to form plated through holes that would eventually connect circuits on the front and back of the reaction detection chamber. A 3-5 µm thick layer of 1827 photoresist was then spun onto both sides of the LCP. The front and back circuit artwork was then aligned to the plated through holes and imaged onto the 1827 using UV (365 nm) light. Resist was developed before etching with 48° for 2 min to remove unwanted copper. The LCP containing the copper circuit was washed and allowed to dry before undergoing electroless plating with tin (Immersion Tin Plating, Dalpro, St. Louis, Mo.) and cutting to size.

Figure 3:
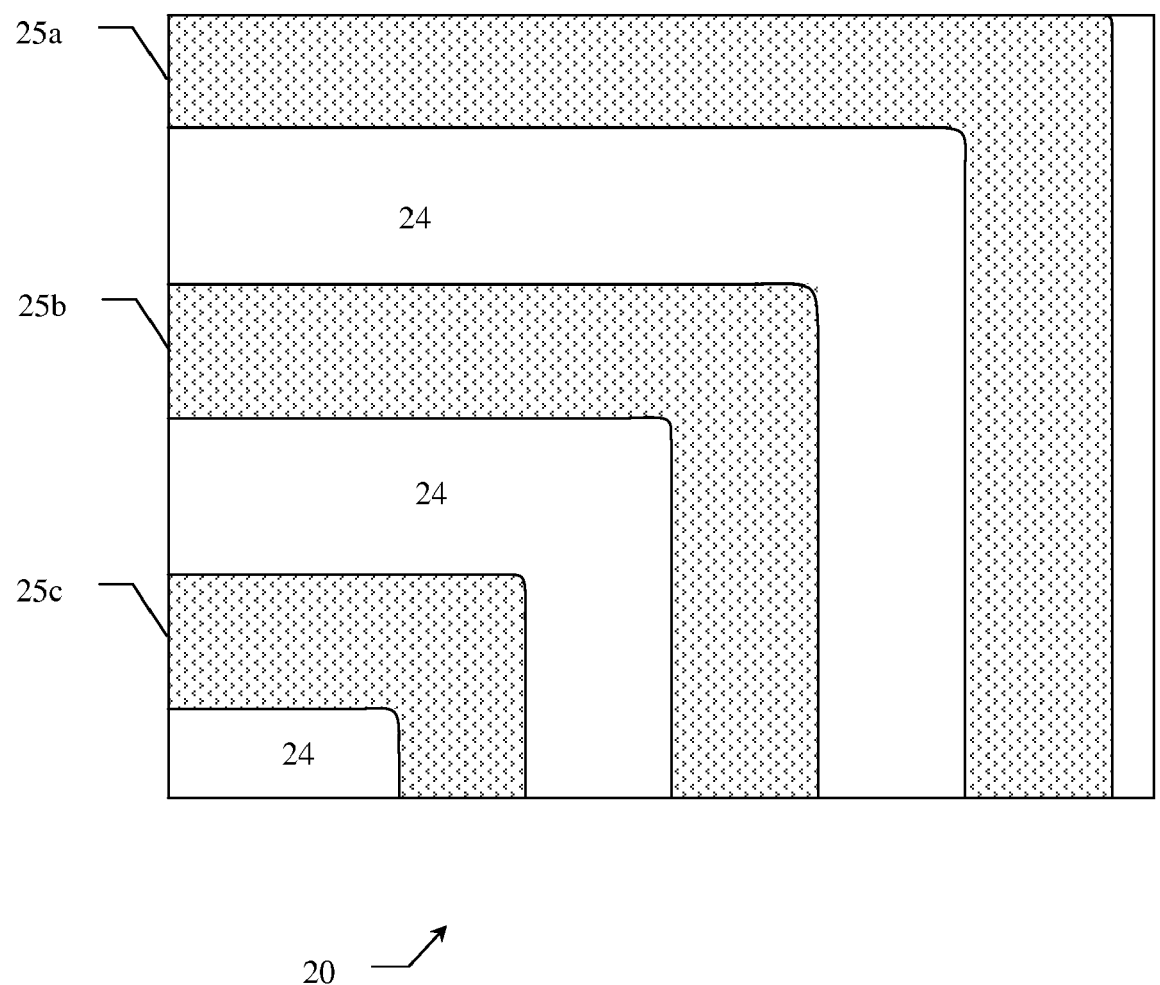
FIG. 3 is a magnified image of resistive heater circuitry.

Heater 22 is a resistive style heater composed of a series of connected concentric traces (25*a*), (25*b*—126.3 µm and 25*c*—119.6 µm) that are approximately 120 µm wide formed on the exterior surface 24 of chamber 20 (FIG. 3). To ensure adequate operation, the resistance of the heater was set to >5Ω.

The fluorometer was constructed by mounting a 567 nm reflective green color sensor and a 470 nm blue LED to the LCP circuit. To prevent saturation of the photo-detector the colour sensor circuit was designed to inactivate the incorporated 567 nm LED. Following attachment to the LCP a small black plastic frit (3.2 mm diameter×3.2 mm high) containing a 1.5 mm diameter hole was glued over the top of the detector portion of the color sensor to ensure proper alignment and spacing of the glass capillary with the photo-detector. The LCP circuit containing the resistive heater and attached LED was folded around a 3.2 mm cylindrical mandrel and joined using polyimid tape. Prior to assembly, a small bead of epoxy resin was run around the outside of the attached frit prior to its insertion into the end of the cylinder. A 45 mm long piece of black 6.35 mm diameter shrink-wrap tubing was then placed over the construct and heated to form a light tight conformal package.

Figure 4:
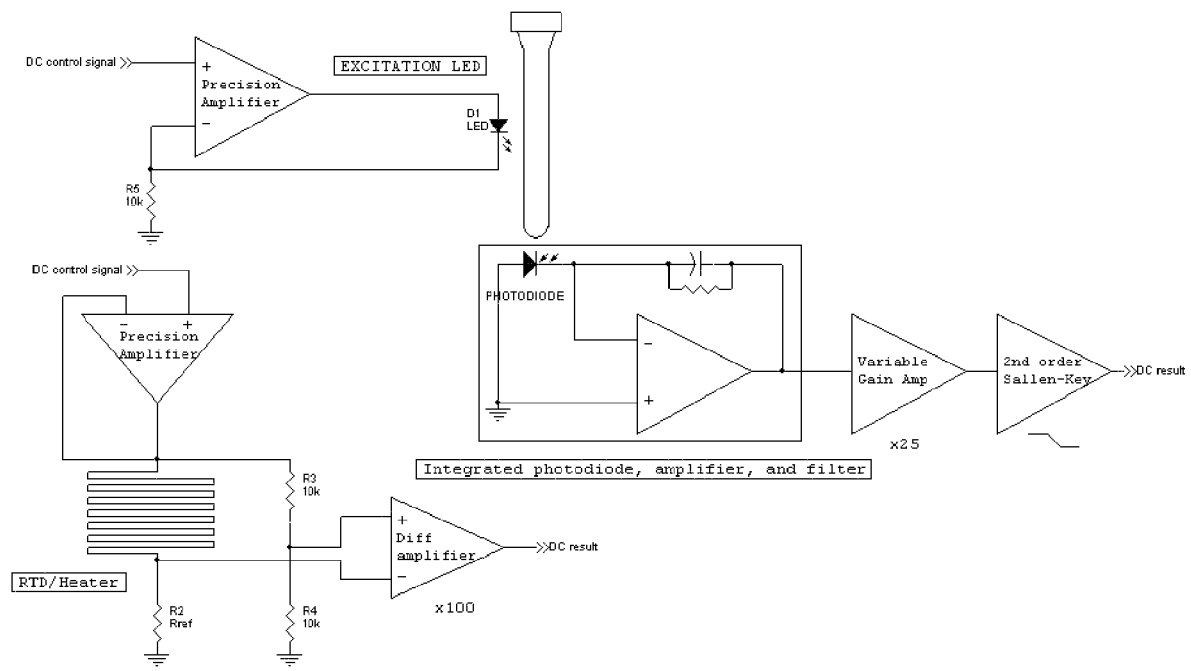
FIG. 4: Block diagram of the heater and fluorometer control electronics.
Figure 5:
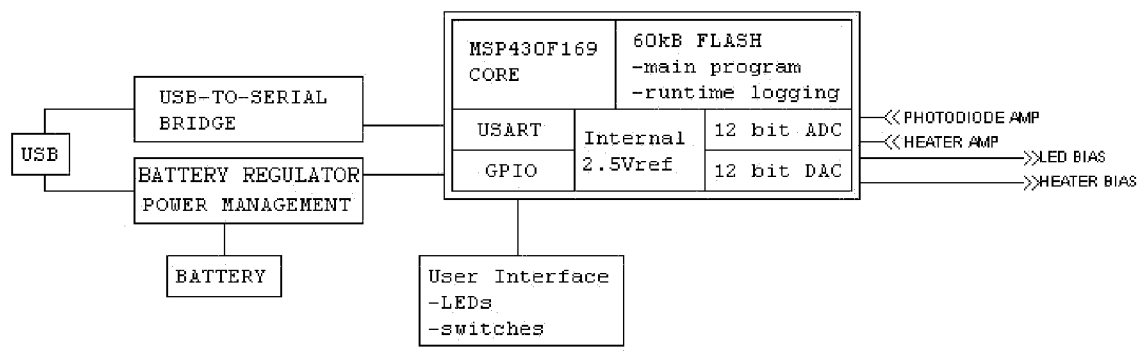
FIG. 5: Functional routing of systems through the MSP430 microcontroller.

Electronic design schematics of the instrument are shown in FIGS. 4 and 5. The copper heating element serves as a linear resistive temperature device (RTD) that monitors the immediate surface temperature and allows for a no-dead-time control loop. To achieve thermal regulation the resistance of the heater is monitored and the voltage bias on the bridge through a power amplifier is controlled. Calibration of the NASBA reactor is required only at the operating point (~41° C.). However, if required, a multipoint linear regression can be performed to provide accurate temperature data from the resistance calculations for other applications. The blue LED intensity is controlled by a programmable constant current source in the microampere range. The detector's internal amplifier is supplemented by an external non-inverting amplifier, followed by a Sallen-Key second-order low-pass filter which aids in increasing the signal to noise ratio.

To decrease power consumption, an ultra low power mixed signal microcontroller is used to control subsystems in the analyzer. The integrated analog subsystem of the microcontroller performs the analog to digital conversion to read the voltages from the circuitry, as well as the digital to analog conversion to change the bridge bias and LED bias.

Software controlling the instrument was written in C, in the IAR Development Studio (IAR Systems, Marlborough, Mass.). The user of the instrument has access to a number of menus through HyperTerminal (Hilgraeve, Monroe, Mich.), or any other serial interface that enables reaction parameters or results to be varied, calibrated or downloaded. The USB connection provides both communication and power to the instrument, as well as implementing automatic baud rate recognition upon insertion. Reaction parameters and system preferences are stored in low power FLASH memory on the MSP430 microcontroller and recalled automatically upon power-up. A real time clock routine running on a 32 kHz watch crystal maintains the time and date and provides time stamps for the data and accurate timing for the reaction. Time stamped fluorescence values are read and stored to low power FLASH memory over minute intervals during a 60 min amplification window. The process subroutine executes in programmable intervals that are characteristic for the heat control loop, in which the resistance measurement is made and a new bias value is calculated for the heater. This single timing parameter can control the heater response from underdamped to overdamped with overshoot response. To provide feedback to the user via the LED interface, fluorescence values are normalized by averaging data from the first 10 minutes of each reaction, each subsequent fluorescence value is then divided by this value. A positive reaction is determined by the illumination of a red LED when the normalized fluorescence reaches a user-determined threshold value during the 60 min reaction. A negative reaction is not determined until the window has expired.

The instrument is powered by one internally mounted CR17450E-R 3V disposable Lithium battery (Sanyo, Chatsworth, Calif.). Alternatively power can be supplied via a USB connection to a personal computer. The analog electronics are supplied through a high-efficiency power supply that is switched off to conserve power during standby. The analog subsystem of the microprocessor is also turned off during this time, reducing current consumption to less than 250 uA active. The processor then enters a low power mode than allows execution of the real time clock functions at an average of 40 uA while waiting for a switch on the user interface to be pressed or a command through the USB interface.

Calibration of the instrument was performed by monitoring the temperature of a NASBA reaction using a Type K hypodermic thermocouple (Omega, Stamford, Conn.) connected to a dual channel digital thermometer (Fisher Scientific, Hampton, N.H.) and varying the resistance values for the heater. The heater resistance that obtained a temperature of 40.5±0.5° C. was stored to non-volatile memory. RT-NASBA reactions were prepared in 30 µl volumes using the Nuclisens Basic Kit (bioMerieux, Durham, N.C.) and previously described primers and molecular beacon specific for the detection of *Karenia brevis* and 1 pg of in vitro transcribed *K. brevis* RNA. Additional no template control (NTC) reactions were performed by substituting the RNA with RNase free water. For the hand-held instrument, RT-NASBA reactions were performed in 20 µl LightCycler Capillaries (Roche Diagnostics, Indianapolis, Ind.). Control reactions were performed in standard 200 μl PCR tubes (Bio-Rad, Hercules, Calif.) using the Nuclisens EasyQ system (bioMerieux, Durham, N.C.). Reactions were run for 60 minutes in both the laboratory based EasyQ system and the hand-held sensor. Following amplification, comparative amplification plots were generated by two methods: 1. Graphing the normalized fluorescence values over time, and, 2. Calculating the relative change in fluorescence by subtracting each fluorescence value with the one prior to it (e.g. minute 2–minute 1; minute 3–minute 2 . . . etc) and graphing the result over time.

Figure 6:
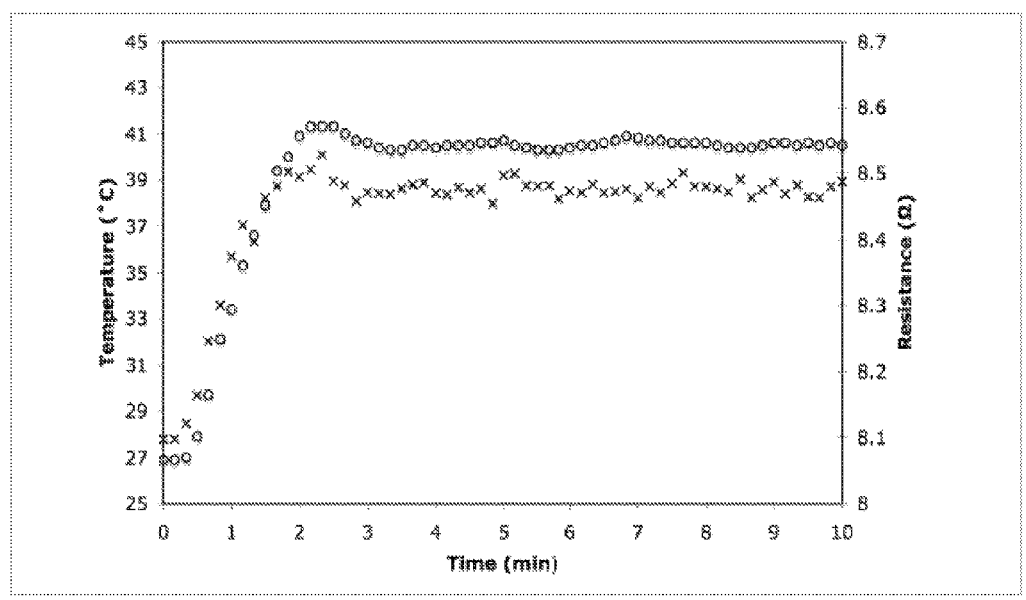
FIG. 6: Heating characteristics of the LCP reaction/detector chamber. Temperature (o) readings were taken every 10 seconds over a 10 minute period. Resistance values (x) are the average of 40 readings taken over 10 seconds.

During heating from ambient temperature to 41° C., the maximum power draw of the entire system was 150 mA. Once stabilized the instrument used 90 mA operating current to maintain an operating temperature of 40.5±0.5° C., the majority of this power consumption is required by the heater, as total current draw of the control electronics is 1 mA. To maintain the waveguide nature of the capillary, the reaction/detection chamber was designed to avoid contact with the capillary. Additionally, to prevent damage to the RTD from repeated insertion and removal of reaction vessels, the reaction chamber was constructed so that once folded, the heater circuit was positioned on the external side of the chamber (FIG. 1a). Despite the physical separation of the heater from the capillary, the reaction chamber is capable of heating a NASBA reaction from room temperature (~26° C.), to the amplification temperature of 40.5±0.5° C. in under 3 min (FIG. 6). This ramping rate is comparable to the ~9° C. min−1 temperature increase observed in previously described hand-held NASBA reactors. Concomitant measurement of the heater resistance values indicates a close relationship between the surface temperature of the heater and the sample temperature indicating efficient radiant heat transfer (FIG. 6)

Previously described thermo-regulated hand-held fluorometers have much higher energy consumption (~300 mA at an operating temperature of 41° C.). This increases the sensors form-factor when packaged with a power source and limits the number of assays that the instrument could perform to one sample under battery power. The RT-NASBA analyser described here is powered by one 2400 mAh, 3 V12 lithium battery that provides enough power to perform approximately 238 16, 1 hour NASBA assays.

Figure 7:
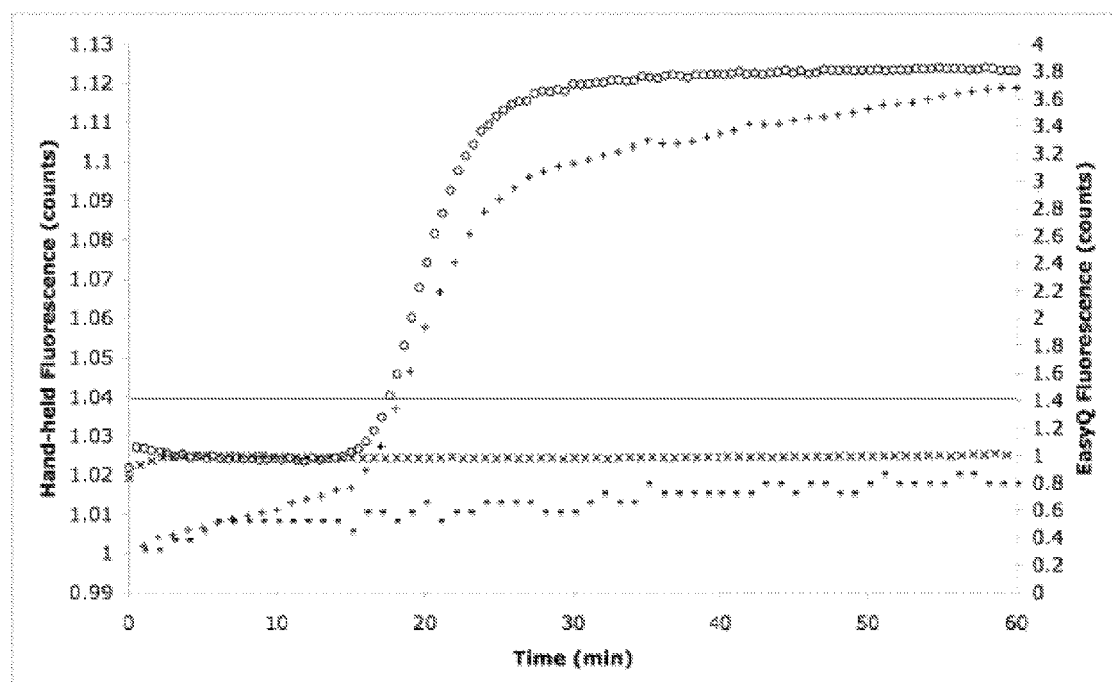
FIG. 7: Typical comparative amplification plots of duplicate reactions performed on the hand-held detector and the laboratory based EasyQ system. The solid line represents the TTP threshold value for the hand-held (1.04) and EasyQ (1.4) systems respectively.
Figure 8:
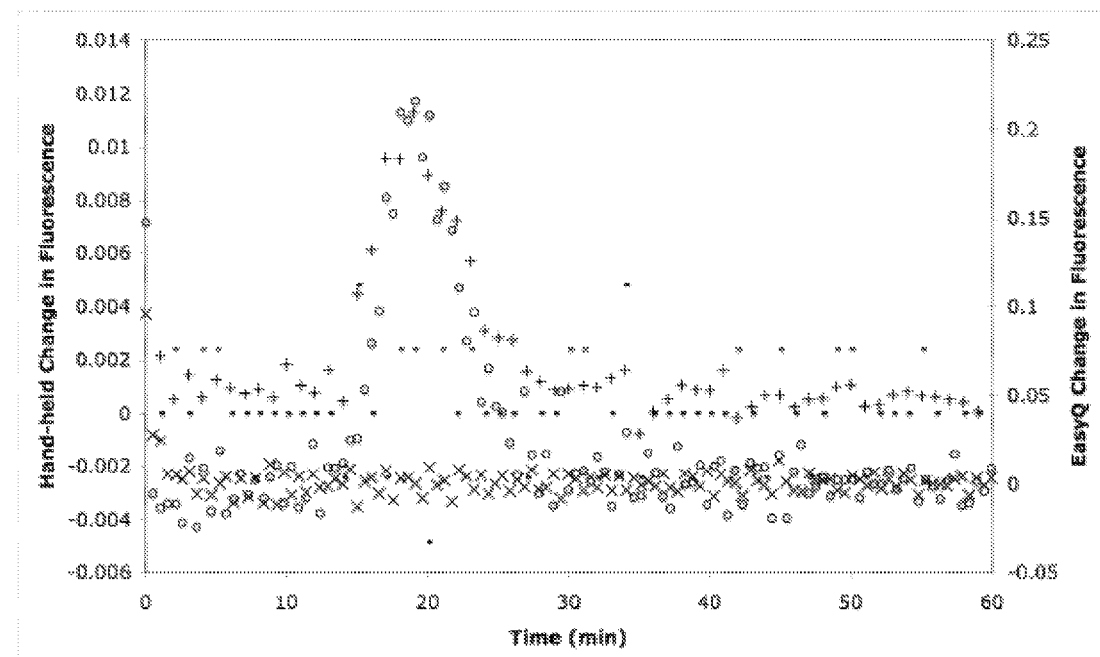
FIG. 8: Comparison of the relative change in fluorescence to provide a nonbiased calculation of TTP. EasyQ no template control (x); EasyQ 1 pg RNA (o); Handheld no template control (−); Hand-held 1 pg RNA (+).

Despite the optical band-pass filter on the photo-detector being at the higher range of the fluorescence spectra of a molecular beacon labeled with 6-carboxyfluorescein (FAM) (max. emission at 515 nm), the instrument is sufficiently sensitive and has enough dynamic range to detect amplification occurring in the RT-NASBA reaction (FIGS. 7 and 8). Example amplification plots comparing reactions containing 1 pg of in vitro transcribed RNA and no-template controls performed in the hand-held instrument and the laboratory based EasyQ system are shown in FIG. 4a. Using the traditional method of calculating TTPs based on a fluorescence threshold (e.g. hand-held—1.04 counts; EasyQ—1.4 counts), less than one minute variation in Time To Positivity (TTP) values (handheld, ~18.3 min; EasyQ, ~17.5 min) were observed between instruments, which can be attributed to the replicate variability that has been observed in RT-NASBA assays (FIG. 7). However, by plotting the relative change in fluorescence over time it can be seen that the response of both instruments mirror each other with peak fluorescence in both instruments occurring at 19 min (FIG. 8). This method represents an unbiased method of determining the actual TTP as it provides the inflection point where the change in fluorescence is at its greatest. Prior to this method TTP threshold values were calculated subjectively by the operator and were subject to variation between assays.

Additionally this method also removes issues of comparing assays run on different instrumentation that have different scales and dynamic ranges. Examination of the amplification plots from the hand-held instrument show an increasing drift in fluorescence intensity over time in both NTC samples and samples containing template RNA. The increase in fluorescence is caused by a change in the scattering of light due to a precipitate that forms in the NASBA chemistry. The system, as tested, asymmetrically heats the capillary as it does not contain a heated lid and the precipitate is presumably formed as a result of evaporation. However, the fluorescence drift does not adversely affect results of any of the NASBA assays used, as samples with template RNA concentrations at the lower limit of detection amplify within the 60 minute window.

By utilizing planar PCB construction techniques and subsequent folding to form a 3-dimensional construct the inventors have developed a novel integrated heated mini-fluorometer. Coupling this sensor portion to custom electronics and packaging has resulted in the development of a small self-contained hand-held device that is capable of performing and reporting RT-NASBA assays. The instrument produces equivalent results to standard laboratory instrumentation but with the added advantage of being readily portable. An additional benefit of the system is the use of a simple LED based interface to give the user real-time feed back as to the status of the reaction, thereby negating the need for an expensive user interface such as a laptop or PDA to be carried 284 into the field. The instrument also provides the ability for in-depth analysis or trouble-shooting to be performed as time stamped reaction parameters (e.g. fluorescence counts, heater resistance, and LED bias) can be obtained in real-time or from FLASH memory via USB connection to a PC. Additionally the invention provides a simple unbiased method to determine TTP values based on the relative change in fluorescence, which will aid in comparison of results from different instrumentation. While the examples contained herein describe a system to perform RT-NASBA, both the instruments operation parameters and level of information stored to memory such as sampling rate, positive threshold level and operation temperature can be altered by the user, which allow other fluorometric assays to be performed within the same platform.

The use of PCB manufacturing techniques to construct the base of the reaction/detection chamber and the subsequent addition of inexpensive LED technology and MEMS based optically tuned photo-detector particularly suits the analytical portion of the sensor to cheap mass production. Furthermore manufacturing the sensor in a planar geometry and conforming it into a 3-dimensional construct obtains production, packaging and design benefits. The modular design of the mini-fluorometer allows it to be easily replaced if damaged, or swapped with a module that detects at a different wavelength. Additionally, the use of PCB based resistive heaters dramatically reduced the energy consumption in the SiP fluorometer compared to previously described IR heater based instruments allowing the instrument to perform multiple reactions, while having reduced form-factor. Further reductions in the overall size of the instrument could potentially be achieved by incorporating the control electronics onto the LCP flexible substrate.

While the pinnacle of point-of-use real-time detection technologies is to allow fast, inexpensive, autonomous diagnosis, it is envisioned that small hand-held analytical instrumentation such as described here will serve as the initial impetus to allow traditional laboratory analysis to be decentralized and taken into the field. This type of analysis will have immediate application in environmental, bio-defense and medical monitoring in areas with limited laboratory infrastructure, such as remote areas where access to traditional laboratory equipment is impractical or unaffordable.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between. Now that the invention has been described,

What is claimed is:

1. A low thermal mass fluorometer, the fluorometer comprising:
   a reaction chamber formed from a flexible printed circuit board substrate;
   a heater integrally formed with the reaction chamber;
   a reaction vessel suspended within the reaction chamber, the reaction vessel positioned to leave a space between the reaction vessel and the reaction chamber;
   a light emitting diode integrated into the reaction chamber positioned to supply fluorescence excitation in substantially orthogonal relation to the longitudinal axis of the reaction chamber; and
   a photodetector positioned to detect fluorescence emission from the reaction chamber.

2. The fluorometer of claim 1, further comprising a control software module; a thermocouple in circuit communication with the control software module; a light emitting diode and an integrated photodetector in circuit communication with the control software module.

3. The fluorometer of claim 1 wherein the flexible printed circuit board substrate is a liquid crystal polymer printed circuit material.

4. The fluorometer of claim 3 wherein circuits for the heater, light emitting diode and photodetector are etched into the liquid crystal polymer material.

5. The fluorometer of claim 1, further comprising an external power supply.

6. The fluorometer of claim 1, further comprising an integrated power supply.

7. The fluorometer of claim 1, further comprising a serial communication module in circuit communication with the photodetector.

8. The fluorometer of claim 7, further comprising an output display in communication with the serial communication module.

9. The fluorometer of claim 1, wherein the photodetector is a 567 nm reflective green color sensor.

10. The fluorometer of claim 1, wherein the light emitting diode is a 470 nm blue light emitting diode.

11. The fluorometer of claim 1, wherein the heater is a MEMS-based linear resistive temperature device.

12. The fluorometer of claim 11 wherein the heater comprises a plurality of connected, concentric traces formed in the exterior of the reaction chamber.

13. The fluorometer of claim 12 wherein the traces formed in the exterior of the reaction chamber are about 120 μm wide.

14. The fluorometer of claim 1 wherein the resistance of the heater is about $\geq 5\Omega$.

15. The fluorometer of claim 1 wherein the reaction vessel is a glass waveguide capillary.

* * * * *